United States Patent [19]

Kühne

[11] 4,303,593
[45] Dec. 1, 1981

[54] PROCESS FOR THE DIMERIZATION OF HEXAFLUOROPROPENE OXIDE

[75] Inventor: Gerhard Kühne, Burghausen, Fed. Rep. of Germany

[73] Assignee: Hoechst Aktiengesellschaft, Fed. Rep. of Germany

[21] Appl. No.: 158,929

[22] Filed: Jun. 12, 1980

[30] Foreign Application Priority Data

Jun. 16, 1979 [DE] Fed. Rep. of Germany ....... 2924385

[51] Int. Cl.³ .............................................. C07C 51/58
[52] U.S. Cl. ............................................... 260/544 F
[58] Field of Search ................................... 260/544 F

[56] References Cited

PUBLICATIONS

Kuehne, Gerhard et al. *Chemical Abstracts*, vol. 91 (1979) #92239q.

*Primary Examiner*—Natalie Trousof
*Assistant Examiner*—L. Hendriksen
*Attorney, Agent, or Firm*—Connolly and Hutz

[57] ABSTRACT

In the dimerization of hexafluoropropene oxide to give oligomeric acid fluorides of the formula

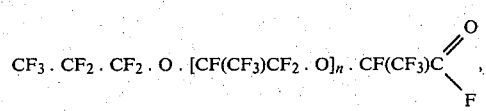

the ratio of the oligomeric constituents formed is directed, in an improved manner, towards the formation of the dimer (n=0) if the reaction is carried out in the presence of a catalyst system which consists of a mixture of a copper (I) compound and a copper (II) compound mixed with a complex-forming agent from the group of the nitriles, isocyanides, tertiary phosphines and cyclic hydrocarbons with 6 to 12 ring atoms and 2 to 3 double bonds in the ring, and an aprotic organic solvent. The dimer is an intermediate product in the synthesis of perfluoropropyl perfluorovinyl ether, the latter being employed as a comonomer in fluorine-containing copolymers.

1 Claim, No Drawings

PROCESS FOR THE DIMERIZATION OF HEXAFLUOROPROPENE OXIDE

The invention relates to a process for the catalytic dimerization of hexafluoropropene oxide, optionally mixed with hexafluoropropene, in the presence of an aprotic organic solvent at temperatures of $-10°$ to $+10°$ C. and under autogenous pressure.

Processes for the polymerization and/or for the oligomerization of hexafluoropropene oxide (hereafter abbreviated HFPO), using various catalysts, are known. These result in oligomeric and polymeric acid fluorides of the formula

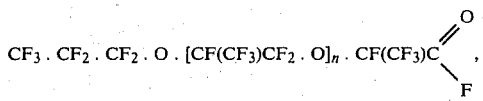

$$CF_3 \cdot CF_2 \cdot CF_2 \cdot O \cdot [CF(CF_3)CF_2 \cdot O]_n \cdot CF(CF_3)C\begin{matrix}\nearrow O \\ \searrow F\end{matrix}$$

wherein n can assume values in the range between 0 and about 25 to 30. Amongst these oligomers, the dimer of HFPO (perfluoro-2-n-propoxypropionyl fluoride, n=0) is of particular interest, since it can be further reacted, by conversion to the alkali metal salt of the homologous carboxylic acid, and its pyrolysis, to perfluoro(propyl vinyl ether), which is a compound of industrial interest. This ether serves as an important comonomer for numerous fluorine-containing copolymers. Hence, it is particularly desirable to direct the oligomerization reaction towards the highest possible proportion of the dimer in the oligomerization product, in order to avoid expensive losses of a dear substance.

It is known (German Patent Specification No. 1,148,750) to employ active charcoal, or high-energy ionizing radiation, for the gas phase polymerization of HFPO. This, however, gives only very small proportions of dimer alongside high proportions of higher oligomers and furthermore, when using active charcoal, the reaction is difficult to carry out reproducibly, because of the fluctuating content of catalytically active constituent in the charcoal. Further, it is known (German Patent Specification No. 1,520,527) that alkali metal fluorides, silver fluoride or thallium fluoride, optionally mixed with other alkali metal halides, have a catalytic action in the oligomerization of HFPO in polar organic solvents. It is true that these catalysts give a molecular weight distribution, of the resulting oligomers, which is somewhat improved in the direction of the dimer, but the distribution is still too broad. Alkali metal fluorides, above all the frequently used cesium fluoride, have the additional disadvantage that they also catalyze the oligomerization of hexafluoropropene (hereafter abbreviated HFP) and thus lead to by-products which are difficult to separate off. It is known that HFP is the starting material for the preparation of HFPO, and it may be therefore present in the latter, mostly in proportions of up to 30% by weight. Separation of the HFP/HFPO mixture is expensive and troublesome, for which reason it is desirable to employ this mixture directly for the oligomerization.

Silver fluoride used as a catalyst for the oligomerization reaction mentioned gives a higher proportion of dimer, but has the disadvantage of a very low solubility in organic solvents and, furthermore, of very high sensitivity towards moisture. Silver nitrate, known from German Offenlegungsschrift No. 2,026,669, is also a relatively cheap and effective catalyst, but when it is used the formation and liberation of nitrous fumes, and, as a result, the formation of undesired fluorine-containing nitroso compounds, must be tolerated. Furthermore, all silver catalysts are lightsensitive, and this causes colloidal silver to separate out, which is a disadvantage.

Known organic functional compounds containing elements of main groups V and VI of the periodic table as oligomerization catalysts for HFPO, such as quaternary salts of nitrogen, phosphorus and arsenic (German Patent Specification No. 1,645,114), tertiary amines and amine oxides (German Patent Specification No. 1,645,115) and sulfonium halides (German Offenlegungsschrift No. 2,614,332) have the disadvantage that they form organic by-products which can only be removed from the product mixture with great difficulties and which, in a continuous process, partially accumulate in the reaction vessel.

Accordingly there remains a need for a catalytic process for the oligomerization of HFPO using a catalyst which should be as selective as possible, that is to say which in particular does not catalyze the oligomerization of HFP, which is easy to handle, which gives a high yield of dimeric product alongside very little isomerization product and higher oligomerization products, which itself does not give any by-products which are undesired and, in particular, difficult to remove, and which, finally, should itself be easily removable from the product mixture and hence reusable.

This can be achieved by a process of the initially-mentioned type which is characterized in that a composition containing (a) a mixture of a copper(I) compound of the formula $Cu_mX$ and a copper(II) compound of the formula $Cu_{m/2}X$, wherein $X=0$ or an anion and m denotes the valency of X, in the weight ratio of 70:30 to 95:5 and (b) a complex-forming agent from the group of the nitriles of the general formula

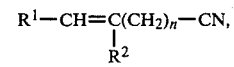

$$R^1-CH=C(CH_2)_n-CN,$$
$$\phantom{R^1-CH=C(}|\phantom{CH_2)_n-CN,}$$
$$\phantom{R^1-CH=C(}R^2\phantom{H_2)_n-CN,}$$

wherein $R^1$ and $R^2$, which are identical or different, denote H, CN or an alkyl radical of 1 to 6 C atoms and one of these alkyl radicals $R^1$ or $R^2$ can optionally be substituted by a CN group, and wherein $R^1$ and $R^2$ can also be linked to form a cyclic alkylene group with 3 to 10 C atoms, and wherein furthermore n denotes an integer from 0 to 5, the isocyanides of the general formula $R^3NC$, wherein $R^3$ denotes an alkyl radical, a cycloalkyl radical, an aralkyl radical or a mononuclear or binuclear aryl radical which is optionally substituted by 1 to 3 $CH_3$ groups, the tertiary phosphines $R^4R^5R^6P$, wherein $R^4$, $R^5$ and $R^6$, which may be identical or different, denote an alkyl radical, a cycloalkyl radical, an aralkyl radical or a mononuclear or binuclear aryl radical which is optionally substituted by 1 to 3 $CH_3$ groups, or the cyclic hydrocarbons with 2 or 3 double bonds and with 6 to 12 C atoms in the ring, or in bicyclic or tricyclic ring systems, or mixtures of these complex-forming agents, is used as the catalyst for the dimerization of HFPO, optionally mixed with hexafluoropropene, in the presence of an aprotic organic solvent at temperatures from $-10°$ to +10° C. and under autogenous pressure, the molar ratio of component (a) to component (b) being 1:1 to 1:8.

As salts of monovalent copper, to be employed for component (a), there should especially be mentioned the copper(I) halides, such as the fluoride, chloride and bromide, and also copper(I) carboxylates, such as, for example, the formate, acetate, propionate, butyrate, benzoate, o-nitrobenzoate, monochloroacetate, dichloroacetate and trifluoroacetate of monovalent copper. Preferably, copper(I) chloride and copper(I) oxide are used as component (a). As salts of divalent copper to be employed as component (a) there should especially be mentioned the copper(II) halides, such as the fluoride, chloride and bromide, copper(II) sulfate, nitrate and phosphate, and also copper(II) carboxylates, such as copper(II) acetate, propionate, benzoate and trifluoroacetate. Copper(II) chloride, copper(II) acetate and copper(II) oxide are preferred. The weight ratio of Cu(I) compound to Cu(II) compound in component (a) is in the range from 70:30 to 95:5, preferably from 80:20 to 90:10. The Cu(II) salts in component (a) can carry the same anions as the Cu(I) salts described above. The mixtures can however also consist of different anions, such as, for example, $CuCl+Cu(CH_3COO)_2$. Mixtures of $Cu_2O$ with Cu(II) salt or of CuO with Cu(I) salt are also suitable.

The complex-forming agents to be employed as component (b) are selected from the following group:

Nitriles of the general formula

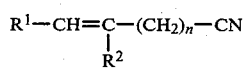

wherein $R^1$ and $R^2$, which can be identical or different, denote hydrogen, a CN group or an alkyl radical with 1 to 6 C atoms, one of which alkyl radicals can be substituted by a CN group.

$R^1$ and $R^2$ can furthermore conjointly assume the meaning of a cyclic alkylene group which possesses 3 to 10 C atoms and hence gives a ring grouping

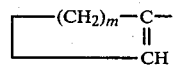

wherein m=3 to 10, preferably 3 to 6, especially 3. Preferably $R^1$ and $R^2$, which may be identical or different, denote hydrogen, a CN group or a methyl or ethyl group, n can be an integer from 0 to 5. Preferably, n=0 or 1. As representatives of this group there may for example be mentioned allyl cyanide, maleodinitrile and fumarodinitrile, 1,1-dicyanoethylene and preferably crotononitrile, methacrylonitrile and especially acrylonitrile.

Isocyanides of the formula $R^3NC$, wherein $R^3$ is a straight-chain or branched alkyl radical, preferably a radical with 3 to 5 C atoms, or a cycloalkyl radical, preferably a radical with 5 to 8 C atoms in the ring, especially a cyclohexyl radical. Furthermore, $R^3$ denotes an aralkyl radical, preferably a benzyl radical, or a mononuclear or binuclear aryl radical which can optionally be substituted by 1 to 3 $CH_3$ groups. The aryl radical is preferably a phenyl, toluyl, xylyl, mesityl or naphthyl radical. Representatives of this group of compounds are, for example, 2-, 3- and 4-methylphenyl isocyanide, 2,3-, 2,4- and 2,5-dimethylphenyl isocyanide, 1- and 2-naphthyl isocyanide and, preferably, phenyl isocyanide, n-propyl isocyanide, tert.-butyl isocyanide and especially cyclohexyl isocyanide.

Tertiary phosphines of the formula $R^4R^5R^6P$, wherein $R^3$, $R^4$ and $R^5$, which may be different or, preferably, identical, denote a straight-chain or branched alkyl radical, preferably an alkyl radical with 1 to 5 C atoms and especially with 3 to 5 C atoms, a cycloalkyl radical, preferably a cyclohexyl radical, an aralkyl radical, preferably a benzyl radical, or a mononuclear or binuclear aryl radical, the aryl radical being optionally substituted by 1 to 3 $CH_3$ groups. This aryl radical is preferably a phenyl or a toluyl radical. Examples to be mentioned from this group of compounds are trimethylphosphine, triethylphosphine, tripropylphosphine, triisopropylphosphine, tributylphosphine, triisobutylphosphine and tri-tert.-butylphosphine, as well as tricyclohexylphosphine, tribenzylphosphine, tri-(o-, p- or m-)toluylphosphine and in particular triphenylphosphine.

Finally, possible complexing agents are also cyclic hydrocarbons with 2 or 3 double bonds and with 6 to 12 C atoms in the ring, this ring structure being tricyclic, bicyclic or, preferably, monocyclic (benzene is excluded). Particularly preferred representatives are cycloocta-1,5-diene and cyclododeca-1,5,9-triene.

The complex-forming agents mentioned can also be employed in the form of mixtures, in which case the individual representatives in such a mixture can belong either to different groups from those mentioned above or, preferably, to the same group.

The mixture of Cu(I) compound and Cu(II) compound of component (a) and complex-forming agents of component (b) is employed, in the catalyst system according to the invention, in a molar ratio of from 1:1 to 1:8, preferably from 1:1 to 1:4.

The amount of component (a) should be between 0.1 and 3 mole % (depending on the size of the batch and the cooling capacity of the reactor), relative to the amount of HFPO employed. In the batches of 25–50 kg of reaction mixture used in industrial practice, the amount of component (a) employed is between 0.8 and 1.0 mole %.

The process according to the invention is carried out in the presence of an aprotic organic solvent which should possess sufficient capacity to dissolve the catalyst system and should not react with HFPO and with the reaction products. Such solvents are essentially polar organic solvents (non-polar solvents can be employed as a mixture with polar solvents), such as, for example, acetonitrile, propionitrile, benzonitrile, nitrobenzene, pyridine, quinoline, N-methylpyrrolidone, tetramethylurea, dioxane, nitroethane, dimethylformamide, dimethylacetamide, dialkyl sulfones and sulfolanes. Other solvents to be mentioned are the dialkyl ethers (preferably with methyl, ethyl and propyl radicals) of ethylene glycol and propylene glycol and of the corresponding diglycols, triglycols and polyglycols, including the mixed polyglycols containing ethylene oxide units and propylene oxide units, and also low-boiling, especially aliphatic, esters.

The solvents mentioned, or mixtures of such solvents, are employed in an amount of 5 to 30% by weight, preferably 5 to 15% by weight, relative to the total reaction mixture.

The process according to the invention is carried out at temperatures between −10° and +10° C., preferably between −5° and +5° C. The temperature ranges mentioned are averages and are not absolutely critical;

rather, it is also possible to go slightly above or below these temperatures during the reaction. The temperature can also be allowed to rise or fall, within the stated range, during the reaction. At the stated reaction temperatures of between −10° and +10° C., a pressure of 2 to 4.5 bar builds up in the reaction vessel as a result of the introduction of HFPO and as a result of the presence of the catalyst solution; preferably, the process is carried out at 2.5 to 3.5 bar autogenous pressure. Since HFP has a boiling point of −28.3° C. under normal pressure (HFPO −28.5° C.), these conditions are virtually the same when mixtures of HFPO/HFP are present.

Industrially, the dimerization process according to the invention is advantageously carried out in a stirred pressure vessel made from stainless steel (for example having a capacity of 50 to 100 l), and equipped with a stirrer, bottom valve and cooling jacket, as well as with the appropriate feed lines. The temperatures should be controlled by temperature-measuring points in the interior of the vessel, in the jacket and in the gas space. Paddle stirrers, anchor stirrers or impeller stirrers can be used; it is advisable to fit a baffle to achieve optimum mixing. The reaction can equally be carried out in a shaken autoclave. The feed line for the HFPO or the HFPO/HFP mixture is provided with a pressure lock, through which the mixture can be metered-in continuously or in portions.

The catalyst solution, that is to say the mixture of copper(I) compound and copper(II) compound of component (a), the complex-forming agent and the organic solvent, is advantageously premixed and then introduced as the first charge into the vessel, or fed to the reaction vessel in portions or continuously through an appropriate feed line. However, it is also possible separately to introduce the mixture of copper(I) and copper(II) compound and complex-forming agent, on the one hand, and the solvent, on the other hand, or the mixture of copper(I) and copper(II) compound and solvent, on the one hand, and the complex-forming agent, on the other hand.

Before the start of the reaction, the reactor is cooled by means of the cooling jacket to a temperature of around 0° C., whilst stirring. The HFPO or the HFPO/HFP mixture is then metered-in, either in portions or continuously, in such a way that the temperature in the liquid phase of the reactor is brought to a value between about −10° and +10° C., preferably between −5° and +5° C.

After completion of metering-in, stirring is continued for 1 to 2 hours at temperatures of about 0° C., after which the pressure in the kettle is released. The off-gas mixture is condensed by passing it through cold traps at temperatures of about −60° C.

After the stirrer has been switched off, the liquid mixture separates into two phases, with the upper phase containing almost exclusively the catalyst constituents and the organic solvent, whilst the dimeric reaction product and the oligomeric by-product formed constitute the lower phase. The upper phase can remain in the reaction vessel and can, after topping up with the requisite amount of catalyst, be employed directly for the next reaction; the lower phase is drained off through a bottom valve.

The technical advantage of the catalyst system employed in the process according to the invention resides in particular in the fact that it is simple to re-use for the same reaction, that is to say it is not only suitable for batchwise operation but also for a type of cascade operation with a settling vessel, from which the catalyst solution is recycled to the reaction kettle. Because of the long life of this catalyst system and the low consumption during the reaction, only minor amounts of fresh catalyst solution must be metered into the reaction kettle before each new batch.

It has also been found that the catalyst system according to the invention, when used repeatedly, leads to a shift of the molecular weight distribution, this distribution being in any case advantageous, in the direction of the dimer, so that the process according to the invention is very particularly suitable for continuous operation. An equilibrium state develops under these conditions, in which a high proportion of the desired dimer is formed.

By its re-usability, the catalyst system according to the invention differs advantageously from, in particular, the silver catalysts (which are also advantageous in respect of the oligomer distribution achieved), since these are either employed as AgF or form AgF in the course of the reaction. AgF is however so sparingly soluble in all conventional organic solvents that it can merely be suspended or dispersed in a very fine form therein. This predominant undissolved, merely suspended, portion of the silver catalyst distributes itself, during the phase separation following the reaction, uniformly between the solvent phase and the product phase, and is accordingly discharged with the product. It must be recovered therefrom, which is time-consuming and involved.

It has been found that the addition of Cu(II) salts to component (a) results in an increase in the proportion of dimer in the oligomer mixture, which is surprising since Cu(II) salts and Cu(II) oxide by themselves, in the presence of the complex-forming agent of component (b), exhibit no catalytic activity whatsoever in the oligomerization of HFPO.

Where mixtures of HFPO and HFP are employed, it is furthermore a great advantage that dimerization or oligomerization of HFP is virtually not observed in the process according to the invention. Hence, the entire content of HFP can, without problems, be separated, together with the volatile compounds, from the liquid reaction product, which mainly consists of HFPO dimers, and no additional expensive methods of separation are required.

The examples which follow are intended to illustrate the invention.

EXAMPLE 1

A catalyst solution consisting of
8.0 g of CuCl (=2.0 mole %, relative to HFPO),
2.0 g of CuCl$_2$ (=0.5 mole %, relative to HFPO),
20.0 g of acrylonitrile and
100.0 ml of acetonitrile
is initially introduced into a dry stirred pressure autoclave of 1 l capacity.

The autoclave is cooled to 0° C. and is then charged in portions, each of about 50 ml, with 740 g of a mixture of HFPO and HFP (HFPO content 90% by weight), through a lock system. The metering-in is controlled in such a way that the temperature inside the autoclave remains within the range of 0° to +2° C. The total metering-in time is 3 hours. After a post-reaction time of one hour at 0° C., whilst stirring, the autoclave valve is opened and the volatile constituents are condensed in a cold trap. The 90 g of condensate collected consists of:
75 g of HFP (80% by weight), 12 g of $CF_3CF_2COF$ (16% by weight) and
3 g of other, non-identified, compounds (4% by weight).

The liquid contents are forced out of the autoclave by means of nitrogen, and the upper phase, which virtually only consists of the catalyst solution, is separated from the lower phase. The lower phase amounts to 650 g and consists of:

550.0 g = 84.6% by weight of dimer,
25.3 g = 3.9% by weight of trimer, and
74.7 g = 11.5% by weight of higher oligomers and other compounds, not identified in more detail.

Accordingly, 82.7% of dimer, relative to HFPO employed, are obtained.

A batch run in the same manner, but with a Cu(I) salt:Cu(II) salt ratio of 90:10, that is to say
9.0 g of CuCl (=2.25 mole %, relative to HFPO) and
1.0 g of $CuCl_2$ (=0.25 mole %, relative to HFPO) gives a proportion of dimer of 81.0% by weight, relative to HFPO employed.

EXAMPLE 2

The experiment of Example 1 is repeated with the following catalyst mixture, but under otherwise identical conditions:
4 g of CuCl (=1.0 mole %, relative to HFPO),
1 g of $CuCl_2$ (=0.25 mole %, relative to HFPO),
5 g of cyclohexylisonitrile and
50 ml of acetonitrile After a total reaction time of 4 hours at 0° to +2° C., the autoclave valve is opened and the volatile constituents are condensed in a cold trap. The 155 g of condensate collected consists of:
75 g of HFP (48.0% by weight)
50 g of $CF_3CF_2COF$ (32.3% by weight) and
30 g of other, non-identified compounds (19.7% by weight).

The liquid contents are forced out of the autoclave and left to stand, for the phases to separate. The lower phase, which amounts to 595 g, consists of:
475 g = 80% by weight of dimer,
78 g = 13% by weight of trimer and
42 g = 7% by weight of higher oligomers and other, non-identified, compounds.

71.2% of dimer, relative to HFPO employed, are formed.

EXAMPLE 3

The experiment of Example 1 is repeated with the following catalyst mixture, but under otherwise identical conditions:
8.0 g of CuCl (=2.0 mole %, relative to HFPO),
2.0 g of $CuCl_2$ (=0.5 mole %, relative to HFPO),
ml of cyclododeca-1,5,9-triene and
100 ml of acetonitrile.

After a total reaction time of 4 hours at a temperature of 0° to +2° C., the autoclave valve is opened and the volatile constituents—which were not analyzed in more detail here—are discharged. The liquid contents are collected and the phases are separated from one another. The upper phase consists of virtually pure catalyst solution. The lower phase, totalling 650 g, consists of:
490 g = 75.4% by weight of dimer,
90 g = 13.8% by weight of trimer and
70 g = 10.8% by weight of higher oligomers and other, non-identified, substances.

The yield of dimer is 73.6%, relative to HFPO employed.

EXAMPLE 4

A solution of 1.8 g of Cu(I) acetate (1.88 mole %, relative to HFPO), 0.2 g of Cu(II) acetate (0.14 mole %, relative to HFPO) and 10.3 g of cyclododeca-1,5,9-triene, thoroughly mixed into 30 ml of acetonitrile, is initially introduced into a carefully dried stainless steel stirred pressure autoclave of 300 ml capacity, equipped with a magnetic stirrer, cooling device and safety valve. 140 g of HFPO/HFP mixture containing 93% by weight of HFPO are then metered in through a lock system.

The reaction is carried out for 18 hours at 0° C., whilst stirring. The valve on the autoclave is then opened and the gas is released. The amount collected in a cold trap is 12.0 g, and is composed, to the extent of 80%, of perfluoropropionic acid fluoride.

After separating off the upper phase, 128 g of a reaction product of the following composition are obtained:
92.0 g = 71.8% by weight of dimer,
24.5 g = 19.1% by weight of trimer and
11.5 g = 9.1% by weight of higher oligomers and other, non-identified, products.

The yield of dimer is accordingly 70.6%, relative to HFPO employed.

EXAMPLE 5

1.8 g of $Cu_2O$ (1.61 mole %, relative to HFPO), 0.2 g of Cu(II) acetate (0.14 mole %, relative to HFPO), 7.0 ml of acrylonitrile and 25 ml of acetonitrile are initially introduced into the stirred pressure autoclave described in Example 4, and are mixed thoroughly for 30 minutes by means of the magnetic stirrer. 140 g of HFPO/HFP mixture containing 93% by weight of HFPO are then introduced, in portions over the course of 30 minutes at 0° to +2° C., through a lock system, and the stated temperature is maintained for 16 hours by keeping the autoclave in a thermostatic bath, whilst stirring. The valve on the autoclave is then opened and the gas is released. The amount of gas collected in a cold trap is 10 g and is composed to the extent of 30% of perfluoropropionic acid fluoride, alongside HFP. After separating off the upper phase, 130 g of a reaction product having the following composition are obtained:
100.0 g = 77.0% by weight of dimer,
5.5 g = 4.2% by weight of trimer and
24.5 g = 18.8% by weight of higher oligomers and other, non-identified, substances.

The yield of dimer is accordingly 77.0%, relative to HFPO employed.

EXAMPLE 6

A solution consisting of 1.5 g of CuCl (1.94 mole %, relative to HFPO), 0.17 g of $CuCl_2.2H_2O$ (0.13 mole %, relative to HFPO), 8.6 ml of crotononitrile and 25 ml of acetonitrile is initially introduced into the stirred pressure autoclave described in Example 4. 140 g of HFPO/HFP mixture containing 93% by weight of HFPO are then introduced, in portions over the course of 30 minutes at 0° to +2° C., through a lock system, and the stated temperature is maintained for 16 hours by keeping the autoclave in a thermostatic bath, whilst stirring. The valve on the autoclave is then opened and the gas is released. The amount of gas collected in a cold trap is 25.0 g and is composed to the extent of 60% of perfluoropropionyl fluoride, alongside HFP.

After separating off the upper phase, 115 g of a reaction product having the following composition are obtained:
91.5 g = 79.5% by weight of dimer,
13.4 g = 11.7% by weight of trimer and
10.1 g = 8.8% by weight of higher oligomers and other, non-identified, substances.

The yield of dimer is accordingly 70.2%, relative to HFPO employed.

EXAMPLE 7

A catalyst solution consisting of 1.5 g of CuCl (1.94 mole %, relative to HFPO), 0.17 g of $CuCl_2.2H_2O$ (0.13 mole %, relative to HFPO), 7.5 ml of methacrylonitrile and 25 ml of acetonitrile is initially introduced into the stirred pressure autoclave described in Example 4. 140 g of HFPO/HFP mixture containing 93% by weight of HFPO are then introduced, in portions over the course of 30 minutes at 0° to +2° C., through a lock system, and the stated temperature is maintained for 16 hours by keeping the autoclave in a thermostatic bath, whilst stirring. The valve on the autoclave is then opened and the gas is released. The amount of gas collected in a cold trap is 22.0 g and is composed to the extent of 50% of perfluoropropionyl fluoride, alongside HFP.

After separating off the upper phase, 118 g of a reaction product having the following composition are obtained:
98.0 g = 83.0% by weight of dimer,
8.8 g = 7.5% by weight of trimer and
11.2 g = 9.5% by weight of higher oligomers and other, non-identified, substances.

The yield of dimer is accordingly 75.4%, relative to HFPO employed.

EXAMPLE 8

A previously prepared solution consisting of 1.8 g of Cu(I) trifluoroacetate (1.30 mole %, relative to HFPO), 0.17 g of $CuCl_2.2H_2O$ (0.13 mole %, relative to HFPO), 6.5 g of cycloocta-1,5-diene and 25 ml of acetonitrile is initially introduced into the stirred pressure autoclave described in Example 4. 140 g of HFPO/HFP mixture containing 93% by weight of HFPO are then introduced, in portions over the course of 30 minutes at 0° to +2° C., through a lock system, and the stated temperature is maintained for 16 hours by keeping the autoclave in a thermostatic bath, whilst stirring. The valve on the autoclave is then opened and the gas is released. The amount of gas collected in a cold trap is 14.0 g and is composed to the extent of 30% by perfluoropropionyl fluoride, alongside HFP.

After separating off the upper phase, 126 g of a reaction product having the following composition are obtained:
94.0 g = 74.6% by weight of dimer,
17.5 g = 13.9% by weight of trimer and
14.5 g = 11.5% by weight of higher oligomers and other, non-identified, substances.

The yield of dimer is accordingly 72.3%, relative to HFPO employed.

EXAMPLE 9

A solution consisting of 1.8 g of Cu(I) acetate (1.88 mole %, relative to HFPO), 0.2 g of Cu(II) acetate (0.14 mole %, relative to HFPO), 6.2 g of triphenylphosphine and 30 ml of acetonitrile is initially introduced into the apparatus described in Example 4. 140 g of HFPO/HFP mixture containing 93% by weight of HFPO are then introduced, in portions over the course of 30 minutes at 0° to +2° C., through a lock system, and the stated temperature is maintained for 16 hours, whilst stirring. The valve on to autoclave is then opened and the gas is released. The amount of gas collected in a cold trap is 13.0 g and is composed to the extent of 40% of perfluoropropionyl fluoride, alongside HFP.

The liquid portion of the reaction product can be separated into an upper phase and a lower phase. The lower phase, containing the desired reaction product, amounts to 127 g and has the following composition:
103.0 g = 81.1% by weight of dimer,
11.3 g = 8.9% by weight of trimer and
12.7 g = 10.0% by weight of higher oligomers and other, non-identified, substances.

The yield of dimer is accordingly 79.2%, relative to HFPO employed.

Repeated use of catalyst system

All the upper phases collected in Examples 1 to 9 were each separately once again introduced, in an amount of 25 ml, into the 300 ml autoclave, and 140 g of HFPO/HFP were metered-in over the course of 30 minutes at 0° to +2° C. The reactor contents were left at 0° to +2° C. for 16 hours in a thermostatically controlled bath, whilst stirring, after which the gases were released and collected in a cold trap. In all the experiments, the gaseous constituent ranged from 10 to 30 g. The proportion of dimer had in all batches increased by 2 to 5%.

The upper phase of the reaction mixture can be re-used at least 5 or 6 more times for repeating the oligomerization of HFPO, and in these batches gives a comparably high yield of dimer to that obtained in the first repeat batch with the catalyst system.

From the fourth repeat batch onwards it is advantageous to replenish with from 1 to 5% of the Cu salt employed.

EXAMPLE 10

A previously prepared solution of 1.5 g of CuCl (1.94 mole %, relative to HFPO), 0.17 g of $CuCl_2.2H_2O$ (0.13 mole %, relative to HFPO), 9.0 ml of tert.-butyl isocyanide and 25 ml of acetonitrile is initially introduced into the experimental apparatus according to Example 4. 140 g of HFPO/HFP mixture containing 93% by weight of HFPO are then introduced, in portions over the course of 30 minutes at 0° to +2° C., through a lock system, and the stated temperature is maintained for 16 hours by keeping the autoclave in a thermostatic bath, whilst stirring. The valve on the autoclave is then opened and the gas is released. The amount of gas collected in a cold trap is 15.0 g and is composed to the extent of 35% of perfluoropropionyl fluoride, alongside HFP.

After separating off the upper phase, 125 g of a reaction product having the following composition are obtained:
95.5 g = 76.4% by weight of dimer,
18.0 g = 14.4% by weight of trimer and
11.5 g = 9.2% by weight of higher oligomers and other, non-identified, substances.

The yield of dimer is accordingly 73.5%, relative to HFPO employed.

EXAMPLES 11 TO 20

The experiments recorded in the table which follows are carried out in the apparatus described in Example 4. The complex-forming agents recorded in column 2 are employed in the oligomerization reaction in combination with the mixtures of Cu(I) and Cu(II) compound corresponding to the example indicated in column 3. The molar ratios of the components and the experimental conditions are those used in the earlier example indicated in column 3:

TABLE

| Example | Complex-forming agent employed | Other experimental conditions as in Example | Amount of gas released g | Total amount in g of oligomers in the lower phase | Composition in % by weight | | |
|---|---|---|---|---|---|---|---|
| | | | | | Dimer | Trimer | Higher oligomer |
| 11 | Cyclohexene-3-nitrile | 4 | 20 | 120 | 75.0 | 8.4 | 16.6 |
| 12 | Fumarodinitrile | 6 | 16 | 124 | 76.6 | 12.1 | 11.3 |
| 13 | Allyl cyanide | 4, except that instead of Cu(I) acetate 1.8 g of Cu(I) benzoate are employed | 24 | 116 | 79.4 | 11.2 | 9.4 |
| 14 | Benzyl isocyanide | 6 | 17 | 123 | 73.2 | 16.3 | 10.5 |
| 15 | Toluyl isocyanide | 9 | 22 | 118 | 79.8 | 13.6 | 6.6 |
| 16 | Phenyl-isonitrile | 8 | 18 | 122 | 77.0 | 14.8 | 8.2 |
| 17 | Tri-n-butyl-phosphine | 9 | 25 | 115 | 77.5 | 9.5 | 13.0 |
| 18 | Tri-cyclohexylphosphine | 4 | 24 | 116 | 79.3 | 6.9 | 13.8 |
| 19 | Tri-benzyl-phosphine | 9 | 18 | 122 | 77.1 | 14.7 | 8.2 |
| 20 | Dimethylphenyl phosphine | 9 | 26 | 114 | 78.2 | 9.6 | 12.2 |

I claim:
1. A process for the catalytic dimerization of hexafluoropropene oxide, optionally mixed with hexafluoropropene, in the presence of an aprotic organic solvent at temperatures of $-10°$ to $+10°$ C. and under autogenous pressure, wherein the catalyst employed is a composition containing
(a) a mixture of a copper(I) compound of the formula $Cu_mX$ and a copper(II) compound of the formula $Cu_{m/2}X$, wherein $X=0$ or an anion and m denotes the valency of X, in the weight ratio of 70:30 to 95:5 and
(b) a complex-forming agent from the group of the nitriles of the formula

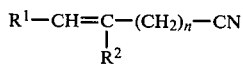

wherein $R^1$ and $R^2$, which are identical or different, denote H, CN or an alkyl radical of 1 to 6 C atoms and one of these alkyl radicals $R^1$ or $R^2$ can optionally be substituted by a CN group, and wherein $R^1$ and $R^2$ can also be linked to form a cyclic alkylene group with 3 to 10 C atoms, and wherein furthermore n denotes an integer from 0 to 5,
the isocyanides of the formula $R^3NC$, wherein $R^3$ denotes an alkyl radical, a cycloalkyl radical, an aralkyl radical or a mononuclear or binuclear aryl radical which is optionally substituted by 1 to 3 $CH_3$ groups,
the tertiary phosphines of the formula $R^4R^5R^6P$, wherein $R^4$, $R^5$ and $R^6$, which may be identical or different, denote an alkyl radical, a cycloalkyl radical, an aralkyl radical or a mononuclear or binuclear aryl radical which is optionally substituted by 1 to 3 $CH_3$ groups,
or the cyclic hydrocarbons with 2 or 3 double bonds and with 6 to 12 C atoms in the ring, or in bicyclic or tricyclic ring systems,
or mixtures of these complex-forming agents, the molar ratio of component (a) to component (b) being 1:1 to 1:8.

* * * * *